Nov. 29, 1949. M. A. HOLMES Plant Pat. 903
ROSE PLANT
Filed Aug. 17, 1948
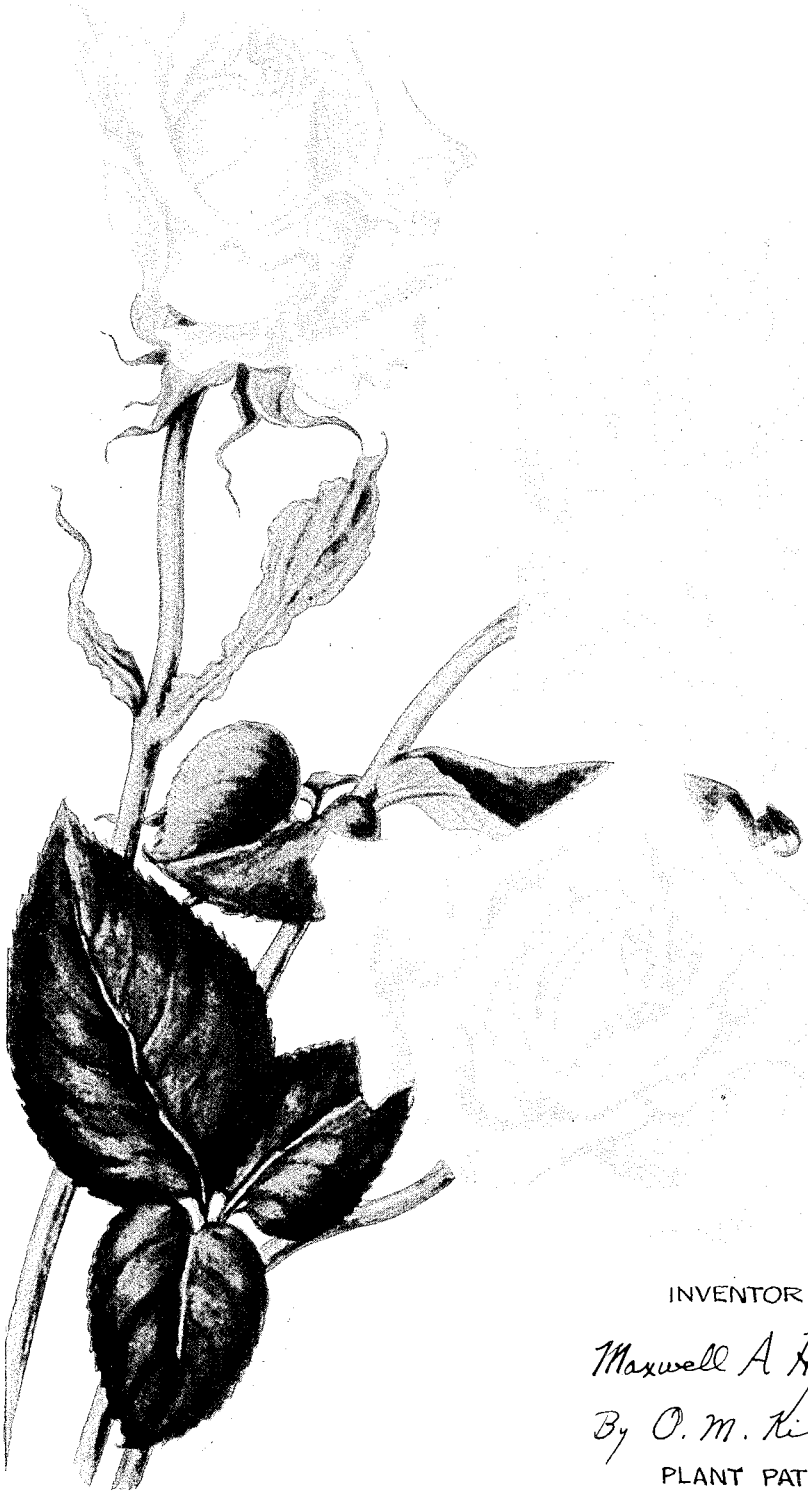
INVENTOR
Maxwell A Holmes
By O. M. Kile
PLANT PATENT AGENT Patented Nov. 29, 1949

Plant Pat. 903

UNITED STATES PATENT OFFICE

903

ROSE PLANT

Maxwell A. Holmes, San Leandro, Calif., assignor to Avansino, Mortensen & Company, San Leandro, Calif.

Application August 17, 1948, Serial No. 44,652

1 Claim. (Cl. 47—61)

My present invention relates to a new variety of hybrid tea rose plant which was discovered by me in the vicinity of San Francisco, as a sport of the variety Pink Delight, formerly known as Vierlanden. Noting what seemed to be outstanding characteristics, particularly as to color, I propagated the sport mutation. After several generations the characteristic features appear to be firmly fixed.

My new variety is similar to its parent in growth except that it produces more branches and consequently is a much freer bloomer. The flower differs from that of its parent particularly in its color and form. The color of the new rose is a clear light pink in contrast with the rose pink of its parent. The bud and flower are larger and fuller than those of the parent, due both to greater petalage and to greater substance of petals. The flower is very long-lasting, due in part to its substance and in part to the clinging ability of the petals. The form of the flower differs in that it is fuller and opens in a more pronounced spiral form.

Illustrations accompanying these specifications show three specimens of the flowers of this new variety in various stages of opening, together with portions of the stem and foliage—all in approximately their true colors.

The illustrations and the following detailed description were made from flowers shipped by air to Washington, D. C., arriving the next day after shipment. Color plate references indicate Ridgway's Color Standards and Nomenclature.

*The plant*

Growth: Strong and vigorous bush. Makes very long, straight canes from a cut or pinch (this being of great value in commercial cut flowers).

Blooming habit: Very free-blooming. Continuous.

Disease resistance: Very healthy and particularly resistant to mildew.

Stems: Very strong and sturdy. Smooth, except that low on the stems there appear a few large sharp thorns which are greenish-white in color and downward-pointing. Internodes are short, bringing the foliage close together. Color is bright shining green, approximately Parrot Green (Plate VI).

Foliage:

*Quantity.*—Abundant.

*Type.*—Usually 3 to 5 leaflets. A characteristic feature of many of the flower stems is that at the base of the peduncle there appear two very small opposite leaflets. The first below this has 3 leaflets.

*Color.*—Rich dark green, approximately forest Green (Plate XVII) on the upper surface and Light Bice Green (Plate XVII) on the under surface.

*Texture.*—Leathery.

*Appearance.*—Neither glossy nor dull, but rich looking. Veining prominent and midrib distinctly lighter.

*Leaf stems.*—Smooth and very short. Lateral leaflets practically sessile.

*Shape.*—Leaflets broadly oval with rounded base and acuminate apex.

*Size.*—Terminal leaflets approximately 2 inches by 3 inches.

*Stipules.*—Very broad and leaflike. Clinging except at points, which are small and straight.

*The flower*

Bud:

*Color.*—Rose Pink to Deep Rose Pink (Plate XII). When outer petals open a little, the edges show Deep Rose Pink.

*Size.*—1½ to 2 inches long. Larger and fuller than its parent, due both to increased petalage and to increased substance of petals.

*Form.*—Urn-shaped.

*Peduncle.*—Short to medium in length. Very strong, holding flowers upright, and never having any weak necks. Same color as stems. Covered with very fine spines, which are more numerous nearer the flower.

*Calyx.*—Sepals broad and slightly branched at sides but with no tendency to be foliaceous.

Flower:

*Form.*—High-centered, usually opening in a pronounced spiral pattern. This stage is held an unusually long time but in the last stages numerous stigmas and anthers are visible. Petals roll back softly as the flower opens.

*Color.*—One of the outstanding features of this rose is the variation of pink tones in the various stages of opening. In the early stages of opening the petals in the outer row are approximately Deep Rose Pink (Plate XII) on the upper surface and Deep Rose Pink (Plate XII) to Pale Rosolane Purple (Plate XXVI) on the reverse side. The inner petals at this stage are Rose Pink on the inner surface (which is visible) and slightly darker pink on the reverse side. In the fully open flower the inner or visible surface of the petals is Cameo Pink (Plate XXVI) with the reverse side slightly darker pink. At this stage numerous yellow stamens and anthers are visible, with a background and frame of the delicate pink petals.

*Size.*—Diameter 4½ to 5 inches, with a depth of about 2 inches in the high-centered stage of opening.

*Fragrance.*—Delicately fragrant.

*Petalage.*—28 to 35 petals.

*Longevity.*—Very good. The flower has the initial ability to hold its petals on the stem for a long time after opening.

Petals:

*Texture.*—Very heavy and substantial but fine in texture. Soft to touch.

*Appearance.*—Silky.

*Shape.*—Outer petals almost round.

*Size.*—Outer petals slightly more than 2 inches in diameter in each direction. Central petals much smaller and more irregular.

Reproductive organs:

*Pistils.*—Many, tightly grouped in center of large pithy ring or platform which is about ½ inch in diameter. Styles short and pink-tinted. Stigmas pale yellow.

*Stamens.*—Emanating from edge of pithy ring, some extending straight outward and others curling toward the pistils. Filaments long (½ inch), pink-tipped, shading to red at base. Anthers large and dark yellow, approximately Yellow Ocher (Plate XV). This arrangement on the wide pithy ring and with the long filaments provides an unusually large yellow center.

Having thus disclosed my discovery, I claim:

The new and distinct variety of hybrid tea rose plant substantially as herein shown and described, characterized particularly by its healthy and vigorous growth; its abundant large dark green foliage; its sturdy stem and peduncle; its relative lack of thorns; its very free habit of blooming; the large full bud; the longevity of the flower; the habit of the flower to open in a definite spiral formation; the large formation of stamens and pistils; and the delicate pink coloring of its large flowers, varying in the different stages as indicated.

MAXWELL A. HOLMES.

No references cited.